United States Patent
D'Amico et al.

(10) Patent No.: US 6,863,073 B2
(45) Date of Patent: Mar. 8, 2005

(54) LAMINAR CRIBOSA PUNCTURE DEVICE, METHODS RELATED TO USE OF SUCH A DEVICE AND METHODS FOR TREATING CENTRAL RETINAL VEIN OCCULSIONS

(75) Inventors: Donald J. D'Amico, Hingham, MA (US); Eugene Lit, Ontario (CA); Paul Hallen, Keller, TX (US); Mark Forchette, Colleyville, TX (US); Werner Maag, Glarus (CH)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 10/136,090

(22) Filed: Apr. 29, 2002

(65) Prior Publication Data

US 2003/0059755 A1 Mar. 27, 2003

Related U.S. Application Data

(60) Provisional application No. 60/287,499, filed on Apr. 29, 2001.

(51) Int. Cl.[7] .............................................. A61B 19/00
(52) U.S. Cl. ..................... 128/898; 604/541; 606/107; 606/166
(58) Field of Search ............................... 606/107, 166, 606/167, 168, 169, 170

(56) References Cited

U.S. PATENT DOCUMENTS

| | | | | |
|---|---|---|---|---|
| 3,618,594 A | * | 11/1971 | Banko | 606/169 |
| 3,659,607 A | * | 5/1972 | Banko | 606/169 |
| 4,759,746 A | * | 7/1988 | Straus | 604/512 |
| 5,013,295 A | * | 5/1991 | Dubroff | 604/38 |
| 5,037,384 A | * | 8/1991 | Chang | 604/28 |
| 5,252,568 A | * | 10/1993 | Chiou | 514/211.13 |
| 5,411,510 A | * | 5/1995 | Fugo | 606/166 |
| 5,669,923 A | * | 9/1997 | Gordon | 606/170 |
| 5,722,428 A | * | 3/1998 | Kaplan et al. | 128/898 |
| 5,738,676 A | * | 4/1998 | Hammer et al. | 606/4 |
| 6,440,729 B1 | * | 8/2002 | Hudson et al. | 435/325 |
| 6,701,169 B1 | * | 3/2004 | Denninghoff | 600/320 |

* cited by examiner

Primary Examiner—Gary Jackson
Assistant Examiner—Charles H. Sam
(74) Attorney, Agent, or Firm—Peter F. Corless; William J. Daley, Jr.; Edwards & Angell, LLP

(57) ABSTRACT

Featured is a device for puncturing tissue of a body, such as the lamina cribosa and methods for treating a CVRO with such a puncturing device. The puncturing device includes a puncture member being generally configured and arranged to locally disrupt tissue proximal an area of the puncture site, to minimize the potential for damage to body parts or tissue immediately adjacent to this area of the puncture site and to facilitate perforation of the tissue at the puncture site. When the lamina cribosa is being punctured, the puncture member is more particularly configured and arranged to locally disrupt connective tissue of the lamina cribosa proximal to and surrounding the central retinal vein while minimizing the potential for structural damage to the central retinal vein. In an exemplary embodiment, the lamina cribosa is repeatedly punctured to strip/locally disrupt connective tissue surrounding the central retinal vein.

10 Claims, 5 Drawing Sheets

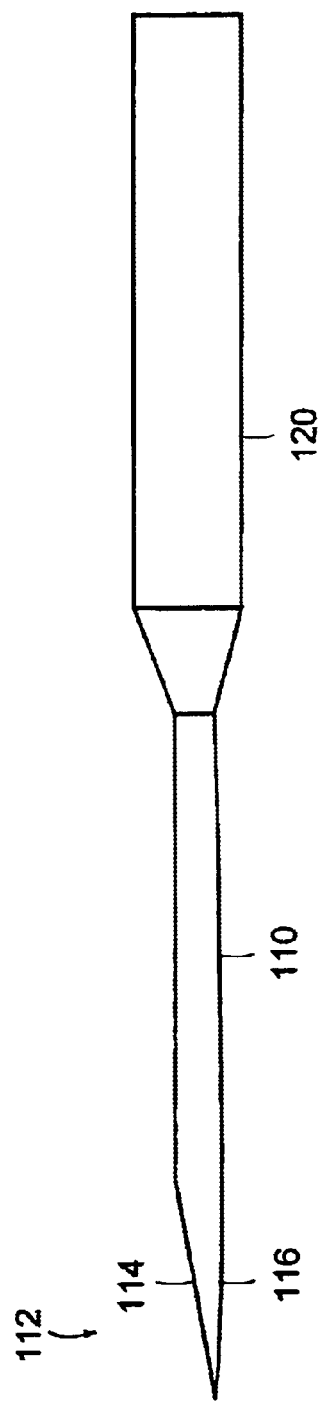
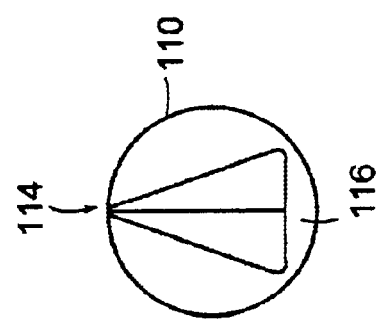

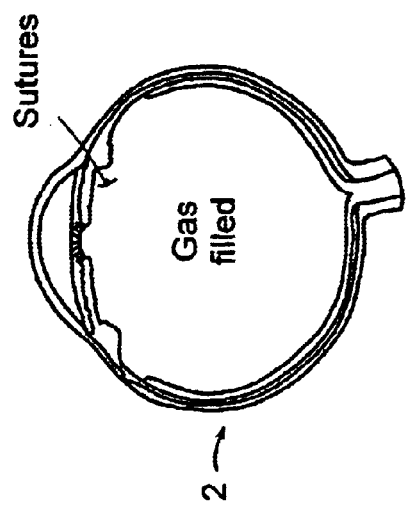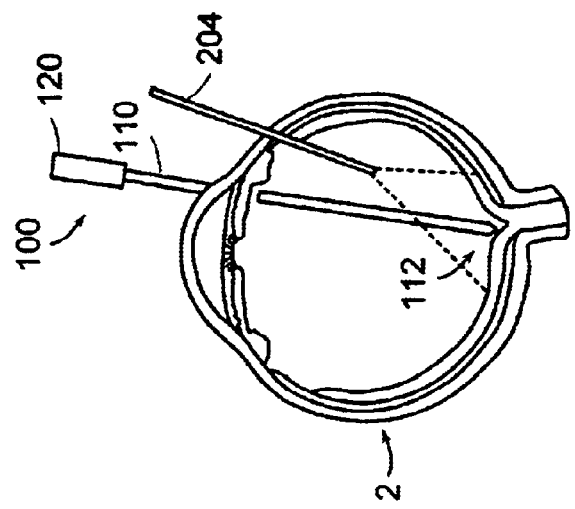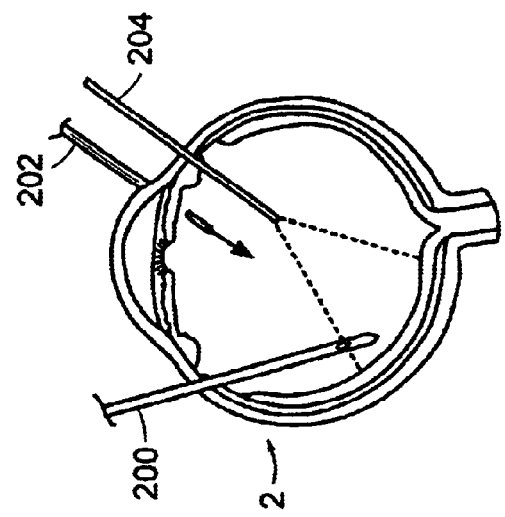

LAMINAR CRIBOSA PUNCTURE DEVICE, METHODS RELATED TO USE OF SUCH A DEVICE AND METHODS FOR TREATING CENTRAL RETINAL VEIN OCCULSIONS

The subject application claims the benefit of U.S. Provisional Application Ser. No. 60/287,499 filed Apr. 29, 2001, the teachings of which are incorporated herein in their entirety by reference.

FIELD OF INVENTION

The present invention relates to devices for puncturing human tissue and more particularly a device for puncturing the laminar cribosa of an eye, more specifically the human eye, as well as methods related thereto.

BACKGROUND OF THE INVENTION

There are a number of diseases or disorders of the eye and/or the optic nerve thereof, including central retinal vein occulsion (CRVO). CRVO is a difficult and often frustrating disease for both the ophthalmologist and the patient. Even in non-ischemic presentations, the majority of patients are left with poor vision, and in those patients with wide-spread capillary non-perfusion (essentially a no-blood flow type of condition), less than 10% of patient's have better than 20/400 vision. Stated another way, CRVO leads to the degradation of the condition of the eye which could ultimately lead to a loss of vision in the afflicted eye. No treatment has been proven to be useful in improving the vision of an eye exhibiting CRVO. The ophthalmologist is usually left to follow the patient, after ensuring adequate systemic work-up, and watch for the development of iris neovascularization.

Neovascularization is the term used to describe the process whereby new blood vessels are formed in the cornea in response to anoxia, the absence of oxygen. Although this might seem beneficial, the formation of such new blood vessels usually results in further degradation of the vision in the affected eye because of the blockage of light and/or the creation of retinal detachments. In any event, and as described below, the CRVO usually occurs in a central retinal vein and thus the formation of additional capillaries or blood vessels do not increase the level of available oxygen to the eye.

As shown in FIG. 1, the sclera of a human eye 2, what is commonly referred to as the white area of the eye, composes about ⅚ of the outside surface of the eye globe. The sclera goes from the limbus in the front or anterior of the globe, which is the junction between the white of the eye and the colored or iris of the eye to the optic nerve located at the posterior of the globe. The sclera is very strong, opaque and inelastic and generally is for maintaining the form and shape of the eye globe and to keep stray light from entering the eye. The sclera varies in thickness and has many blood vessels and nerves passing through it. The area where the optic nerve passes through the sclera is a sieve-like structure called the lamina cribosa.

Histological studies suggest that regardless of the level of perfusion, most or all CRVO's occur from thrombus formation in the central retinal vein at the level of the lamina cribosa. With the relatively denser connective tissue that makes up the lamina cribosa encircling the retinal blood vessels, it is at this level that the luminal diameter of the central retinal vein is the narrowest. Anatomically, thus it is at this level that a literal bottle-neck exists. The resultant increased turbulence in blood flow, and possible increased endothelial cell damage, makes this a theoretically higher risk area for thrombus formation to occur.

It thus would be desirable to provide a new device that can release the constrictive pressure on the central retinal vein by the dense connective tissue encircling or surrounding the central retinal vein and thereby increase the luminal diameter of the central retinal vein in the lumina cribosa, as well as providing new methods to treat a CRVO afflicted eye. It would be particularly desirable to provide such a device and method that can effect such a release in constrictivity with minimal risk to violating the structural integrity of the central retinal vein as well as minimizing the collateral damage to optical nerve fibers. Such collection devices preferably would be simple in construction and such methods are easily adaptable and integratable with existing retinal surgical procedures and techniques.

SUMMARY OF THE INVENTION

The present invention features a device for puncturing tissue of a body, such as the lamina cribosa, so as to locally disrupt this tissue without violating other tissue or vessels also proximal the locus of the device when it is inserted into body (i.e., the puncture site). Also featured are methods for using such a device, in particular methods for treating central retinal vein occulsion (CRVO). Although such a device and methods are particularly useful for treating a CRVO condition of a human eye, such devices and methods are not particularly limited to such applications as well as not being particularly limited to treatment of humans.

A puncturing device according to the present invention includes a puncture member that is generally configured and arranged so as to local disrupt tissue proximal an area of a puncture site and to minimize the potential for damage to body parts or tissue immediately adjacent to this area of the puncture site. Such a puncture member is further configured and arranged so as to minimize damage to tissue in other areas of the puncture site. In a more particular embodiment, the puncture member is generally configured and arranged so as to local disrupt tissue on one side of the puncture site and to minimize damage to tissue on an other side(s) or an opposite side of the puncture site.

In the case where the puncturing device is being used to puncture the lamina cribosa, the puncture member is generally configured and arranged to local disrupt connective tissue of the lamina cribosa proximal to and surrounding the central retinal vein, thereby releasing at least in part the constriction by the surrounding connective tissue. Such a puncture member also is configured and arranged such that such local disruption is accomplished while minimizing potential for structural damage to the wall of the central retinal vein. Additionally, such a puncture member is configured and arranged to facilitate perforation of the lamina cribosa while minimizing potential for structural damage to the central retinal vein by such configuration and arrangement.

In further embodiments, the puncture member is configured and arranged so one edge thereof is a blunt edge to locally disrupt tissue at the puncture site. In a more particular embodiment, the blunt edge is slightly roughened. This is particularly advantageous when puncturing the lamina cribosa because it facilitates stripping away of the connective tissue of the lamina cribosa from the central retinal vein. When puncturing the lamina cribosa, the blunt edge of the puncture member is preferably positioned so as to be facing the vessel wall of the central retinal vein.

The puncture member also is configured and arranged so another edge thereof is configured and arranged so as to present a sharp edge to facilitate perforation of the tissue at the puncture site, such as the perforation of the lamina cribosa. When puncturing the lamina cribosa, the sharp edge of the puncture member is positioned so as to be facing away from the vessel wall of the central retinal vein. This thereby minimizes the potential for damage to the vessel wall.

In more specific embodiments, the puncture member is sized so as to pass through a standard sclerotomy or incision in the human eye and preferably is sized so the puncture wounds have a width in the range of about 400 microns or less, more particularly in the range of about 200 to 400 microns, more specifically in the range of about 300 to 400 microns. In exemplary embodiments, the puncture member is configured and arranged so as to have a relatively blunt tip, a width in the range of about 400 microns or less, more particularly in the range of about 200 to 400 microns, more specifically in the range of about 300 to 400 microns, a length of about 800 to 1500 microns and where the cutting edge or sharp edge extends axially along the length of the puncture member a distance in the range of about 200 mircons or less, more particularly in the range of about 60 to 200 microns and more specifically about 60 microns.

The puncturing device further includes a shaft and a manipulative member, where the shaft mechanically interconnects the puncture member and the manipulative member so the puncture member moves responsive to motion of the manipulative member. The length of the shaft is preferably established so that the manipulative member is remote from the puncture site, particularly a puncture site within a body or body part, such as the intraocular volume of a human eye. In this way, the surgeon or medical personnel can remotely manipulate the puncture member remote from a puncture site. In more specific embodiments, the shaft is sized to pass through a standard sclerotomy or incision in the human eye.

In exemplary embodiments, the shaft is sized is sized so as to have a width on the order of about 1 mm or less or about the width of a standard 20 gauge needle. It is within the scope of the present invention for the manipulative member and correspondingly the puncture member, to be manipulated using any of a number of techniques known to those skilled in the art including, but not limited to manual manipulation by medical personnel as well as robotically.

The puncturing device is composed of any of a number of materials known to those skilled in the art for the particular application, particularly, those materials used for a surgical ocular knife. Further, it is within the scope of the present invention for the various elements or components making up a puncturing device to be made of the same or different materials, for example, the puncture member can be made of one material or a composite of materials and the shaft and manipulative member made of a different material or material composite. Exemplary materials include, surgical stainless steel, diamonds, and composites. The materials selected for use also are preferably capable of being sterilized using conventional industry practices such as gamma irradiation, Ethylene Oxide gas sterilization, E-Beam sterilization, steam, chemical or gas sterilization at the point of use (hospital or surgical center) or at the point of manufacture.

Also featured are methods for use of such a puncturing device, particularly the use of such a device to treat central retinal vein occlusion (CRVO) of an affected human eye. A method for treating CRVO or other ocular blood vessel more particularly includes the steps of positioning the puncture member of such a device proximal the vessel wall of the blood vessel (i.e., either artery or vein), puncturing the lamina cribosa at this location and local disrupting connective tissue of the lamina cribosa in an area of, and proximal to, the puncture site. This process is repeated consecutively until a desired level of release of connective tissue is achieved. In exemplary embodiments, the method includes making a plurality or more of consecutive punctures of the lamina cribosa as herein described to release some of the surrounding connective tissue, thereby allowing the luminal diameter of the blood vessel to be increased.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 2A is a side view of a tissue puncturing device according to the present invention;

FIG. 2B is an end view of the tissue puncturing device of FIG. 2A;

FIGS. 3A–C are cross-sectional schematic views of an eye being treated in accordance with the methodology of the present invention;

DESCRIPTION OF THE PREFERRED EMBODIMENT

Figure 1:
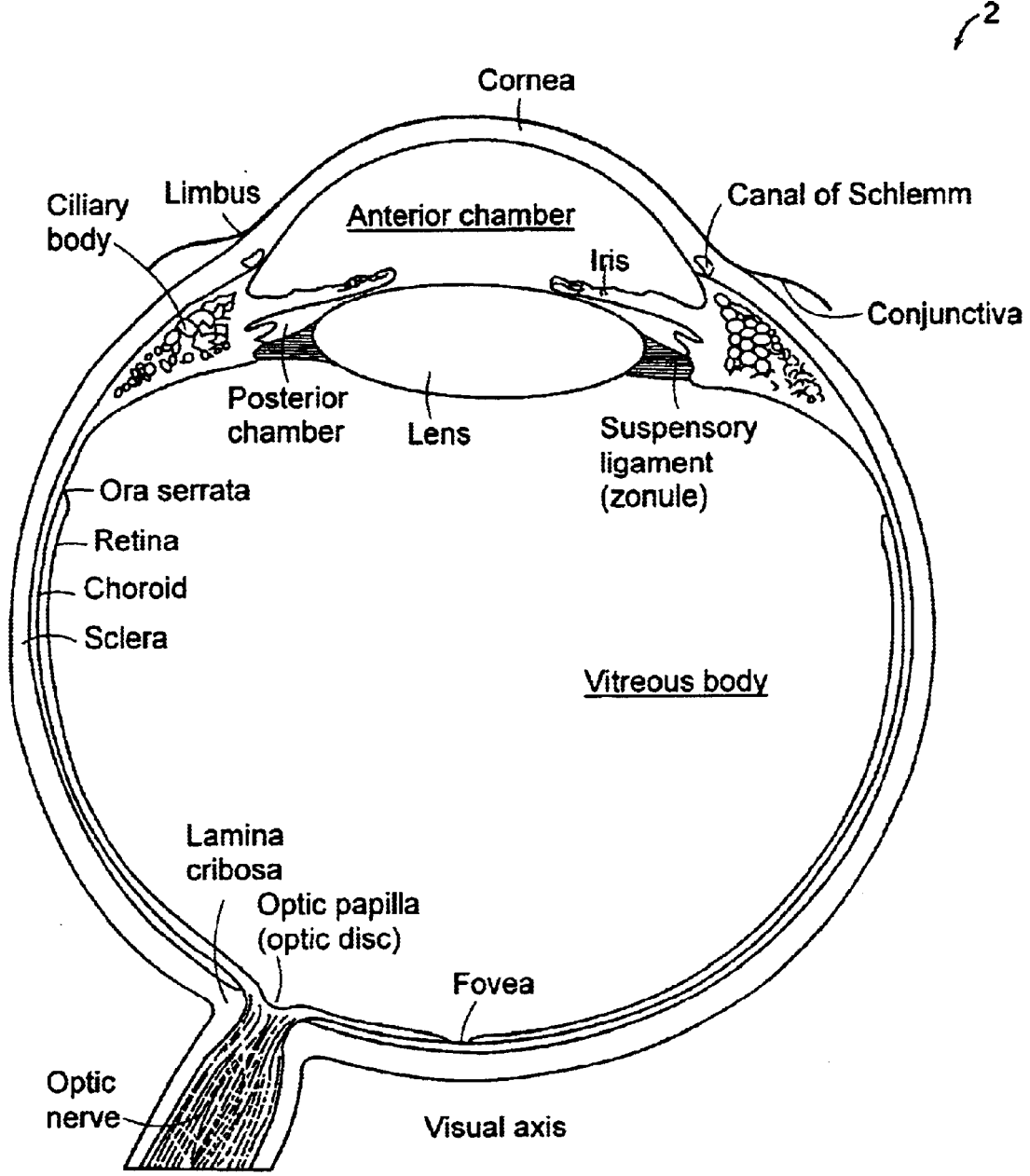
FIG. 1 is a cross-sectional schematic view of a human eye that is not diseased.

Referring now to the various figures of the drawing wherein like reference characters refer to like parts, there is shown in FIG. 2 a puncturing device 100 according to the present invention that includes a shaft 110 and a handle 120 secured to one end of the shaft. The other end, hereinafter the puncturing end 112, of the shaft 110 is particularly configured and arranged to perforate and puncture tissue of a body or body part at a given location, hereinafter referred to as the puncture site. The puncturing end 112 of the shaft 110 is generally configured and arranged so that tissue in one area of the puncture site is locally disrupted and so that there is minimally damage to tissue vessels or body parts in other areas of the puncture site, as well as to tissue, vessels and body parts proximal the puncture site. As hereinafter provided, such configuring and arranging of the shaft puncturing end 112 yields a puncturing device 100 particularly and advantageously adaptable for use in treating a human eye afflicted with a central retinal vein occulsion (CRVO).

In an exemplary illustrative embodiment, and with reference to FIG. 2B, the puncturing end 112 is configured and arranged so one edge thereof is formed as a blunt edge 116. The blunt edge 116 is provided so as to locally disrupt tissue, connective tissue of the lamina cribosa, at the puncture site and in a more particular embodiment, the blunt edge 116 is slightly roughened. This slight roughening is particularly advantageous when puncturing the lamina cribosa because it facilitates stripping away of the connective tissue of the lamina cribosa from the central retinal vein. Such stripping also is accomplished with minimal, to no risk, of damage to the vessel wall of the blood vessel (e.g., vein). When puncturing the lamina cribosa, the blunt edge 116 of the puncturing end 112 is positioned so as to be facing the vessel wall of the central retinal vein.

The puncturing end 112 also is configured and arranged so another edge thereof, is configured and arranged so as to form or present a sharp edge 114. The sharp edge 114 facilitates perforation of the tissue at the puncture site by the puncturing end 112, such as the perforation of the lamina cribosa. The sharp edge 114 also yields a configuration that requires little force to create a relatively small puncture in the lamina cribosa and also lessens the collateral damage to the optic nerve fibers. In more specific embodiments, and as also illustrated in FIG. 2B, the intersections between the sides portions extending between the sharp edge 114 and the blunt edge 116 are preferably rounded or arcuate. When puncturing the lamina cribosa, the sharp edge 114 of the puncturing end 112 is positioned so as to be facing away from the vessel wall of the central retinal vein. This further minimizes the potential for damage to the vessel wall.

In more specific embodiments, the puncturing end 112 and the shaft 110 are sized so as to pass through a standard sclerotomy or incision in the human eye. The puncturing end 112 also is preferably sized so the puncture wounds have a width in the range of about 400 microns or less, more particularly in the range of about 200 to 400 microns, more specifically in the range of about 300 to 400 microns. In exemplary illustrative embodiments, the puncturing end 112 is configured and arranged so as to have a relatively blunt tip, a width in the range of about 400 microns or less, more particularly in the range of about 200 to 400 microns, more specifically in the range of about 300 to 400 microns and a length of about 800 to 1500 microns. The configuration and arrangement of the puncturing end 112 also yields a cutting edge or sharp edge 114 that extends axially along the length of the shaft/puncturing end 110/112 a distance in the range of about 200 microns or less, more particularly in the range of about 60 to 200 microns and more specifically about 60 microns.

As indicated above, the shaft 110 and the handle 120 of the puncturing device 100 are mechanically interconnected to each other such that the puncturing end 112 moves responsive to the motion of the handle. Although a manually manipulated handle is illustrated, this shall not be construed as being a limitation on the manner and mechanism by which the puncturing end 112 can be selectively moved and positioned prior to puncturing and for puncturing of tissue. It is within the scope of the present invention for the shaft 110 to be operably coupled to any of a number of members, devices or apparatuses and/or any of a number of techniques of known to those skilled in the art by which the puncturing end 112 can be positioned proximal a desired site and inserted into the tissue. For example, the shaft 110 can be connected to a apparatus that remotely and robotically manipulates the puncturing end 112.

The shaft preferably has a length established so that the handle 120 is remote from the locus of the puncture site, particularly a puncture site within a body or body part, such as the intraocular volume or posterior globe of a human eye 2 (FIG. 1). In this way, the apparatus, surgeon or medical personnel manipulating the shaft 110 is located remote from the locus of the puncture site. In more specific embodiments, the shaft 110 has a width or cross-section that is set so the shaft passes through a standard sclerotomy or incision in the human eye. In exemplary embodiments, the shaft 110 is sized so as to be have a width on the order of about 1 mm or less or about the width of a standard 20 gauge needle.

The puncturing device 100 is made up of any of a number of materials known to those skilled in the art for the particular application, particularly, including those materials used for a surgical ocular knife. Exemplary materials include, surgical stainless steel, diamonds, and composites. Further, it is within the scope of the present invention for the puncturing end 112, the shaft 110 and the handle 120 making up a puncturing device 100 to be made of the same or different materials. For example, the puncturing end and shaft can be made of one material or a composite of materials and the handle 120 can be made of a different material or material composition. As illustration, the shaft 110 and the puncturing end 112 can be made from a surgical stainless steel and the handle made of a medical quality plastic. The materials selected for use also are preferably capable of being sterilized using conventional industry practices such as gamma irradiation, Ethylene Oxide gas sterilization, E-Beam sterilization, steam, chemical or gas sterilization at the point of use (hospital or surgical center) or at the point of manufacture.

The use of the puncturing device 100 of the present invention can be further understood from the following discussion relating to a method for treating an eye 2 with a central retinal vein occlusion (CRVO) and with reference to FIGS. 3A–C. Reference also shall be made to FIGS. 1–2 specific components or elements of the puncturing device 100 of the present invention not otherwise shown in FIGS. 3A–C and the structure of a human eye 2.

Initially, when treating a CRVO, the user (e.g. medical practitioner) prepares the puncturing device 100 for use. As such, the practitioner removes the puncturing device 100 from its sterile packaging and/or other appropriate action/steps are taken (e.g., sterilization) so that the puncturing device is in a sterile condition and otherwise available for use in connection with the procedure (e.g., surgical procedure) to be performed.

In treating a CRVO the medical practitioner also typically employs a cutting/aspirating instrument 200, a cannula 202 and a light transmitting instrument 204 that are inserted through incisions made in the sclera so one end of each resides intraocular. The light transmitting instrument 204 is configured so light can be projected therefrom to illuminate specific locations within the eye 2 and the retina. As is also known to those skilled in the art, the medical practitioner locates and optically couples a viewing mechanism to the eye 2 so the intraocular volume of the eye 2 including the retina, optic disk and other structures or features within the eye are observable during the procedure.

The cutting/aspirating instrument 200 is disposed within the eye and manipulated so an end thereof is within the vitreous gel therein. Initially, the vitreous gel is removed or aspirated from within the eye 2 by means of the cutting/aspirating instrument 200. As the vitreous gel is being aspirated, the intraocular volume is maintained by a continuous infusion of a fluid, such as a balanced salt solution (BSS), through the cannula 202. This is accomplished using any of a number of techniques known to those skilled in the art.

After such aspirating the vitreous gel/fluid, the medical practitioner inserts the puncturing end 112 of a puncturing device 100 according to the present invention, through one of the incisions made in the sclera for conducting the procedure. By appropriate manipulation of the device handle 120, the medical practitioner positions the puncturing end 112 proximal the optic disk and correspondingly proximal the lamina cribosa. More particularly, the puncturing end 112 is located so that the smooth side or blunt edge 116 of the puncturing end 112 is positioned such that it would be proximal the vessel wall of the central retinal vein during puncturing/insertion and so the cutting or sharp edge 114 thereof is located so it would be positioned away from the vessel wall of the central retinal vein during such puncturing/insertion.

A force is then applied that is generally in a direction along the long axis of the shaft 110 so the puncturing end 112 passes through the lamina cribosa and strips away the connective tissue from the proximal vessel wall thereby locally and selectively disrupting connective tissue of the lamina cribosa. Such stripping/locally disrupting is accomplished while at least minimizing the risk to, and preferably without violating, the integrity of the vessel wall of the central retinal vein. Further such puncturing is accomplished while minimizing the risk of collateral damage to the optic nerve fiber tissue.

The medical practitioner withdraws the puncturing end 112 and repositions the puncturing end at another location and perforates/punctures the lamina cribosa again at the another location thereby stripping/locally disrupting more of the surrounding connective tissue. This repositioning and additional puncturing of the lamina cribosa is continued so as to allow the luminal diameter of the central retinal vein to be increased, preferably an amount sufficient that allows the thrombus to mobilize and pass. In exemplary embodiments, the repositioning and additional puncturing is repeated consecutively so as to strip/locally disrupt a substantial amount of the connective tissue of the lamina cribosa surrounding the central retinal vein, more particularly to completely strip away/local disrupt the connective tissue of the lamina cribosa. In effect, such stripping creates a perivascular space around the central retinal vein. Such increasing of the luminal diameter of the central retinal vein creates a mechanism by which the thrombus is allowed to mobilize thereby leading to the reperfusion of the retina.

Thereafter, the fluid in the intraocular gas is exchanged for a long-lasting gas, such as sulfur hexafluorine or perfluoro propane. After completing the "in eye" portion of the treatment procedure, the inserted instruments 204, cannula 202 and puncturing device 100 are removed from the eye 2 and the incisions therein are appropriately closed by stitching or using other techniques known to those skilled in that art. Thereafter, the puncturing device is disposed of in accordance with normal and usual practices, if it is a one-time use type of device, or is again sterilized in accordance with normal and usual practices if the puncturing device is to be used more than once.

Figure 4:
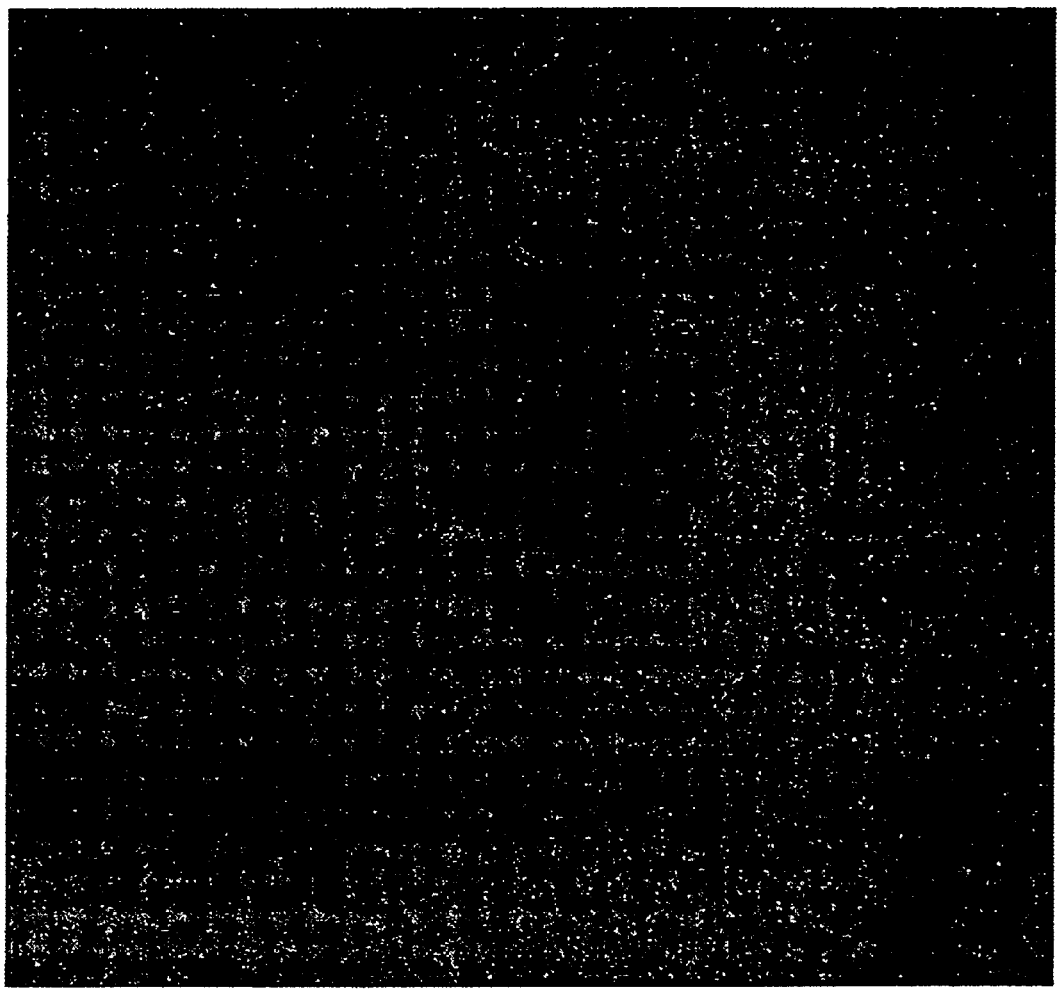
FIG. 4 is a microscopic slice illustrating the optical nerve fibers structure proximal the puncture site.
Figure 5:
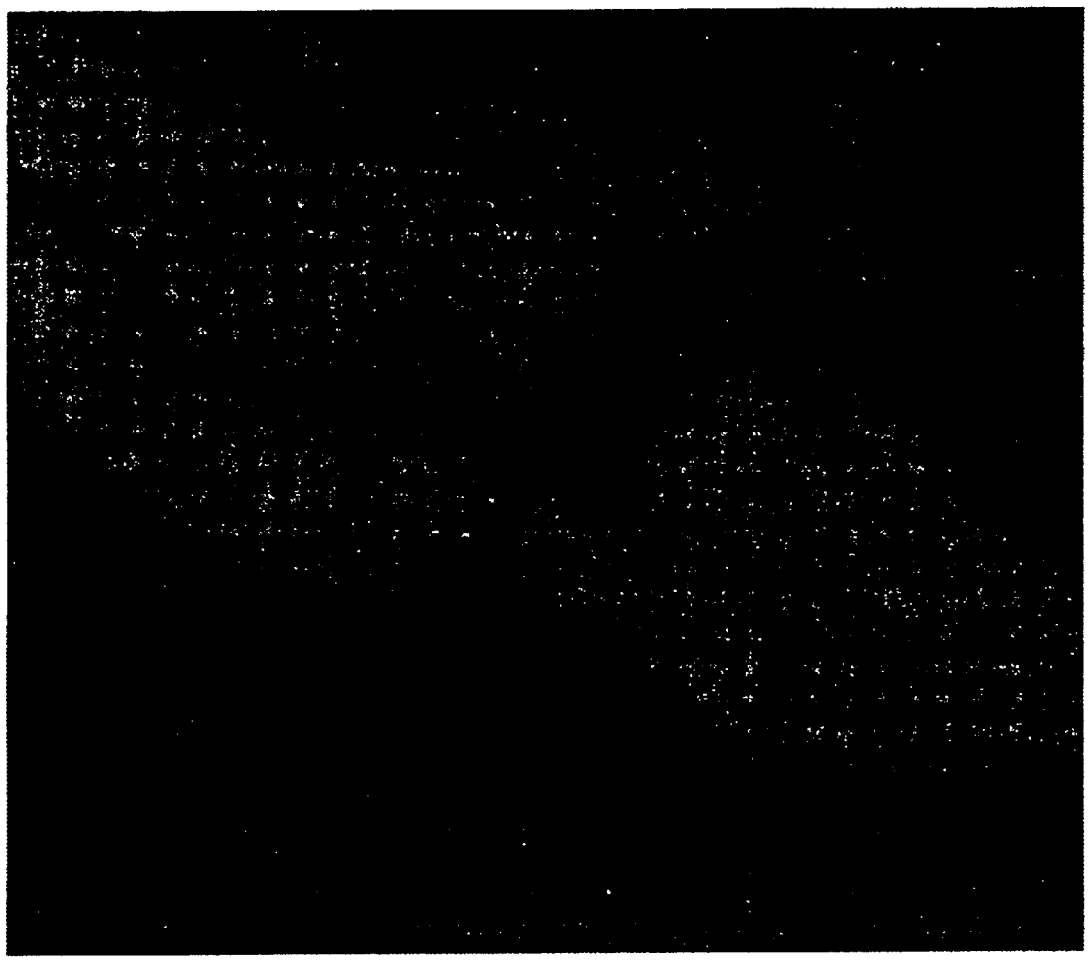
FIG. 5 is a view of an enucleated eye of a rabbit following in vivo laminar puncture via the pars plana, illustrating non-hemorrhaging.

There is shown in FIG. 4 a microscopic slice of the lamina cribosa, the optic nerve tissue and the vessel wall illustrating minimal optic nerve fiber damage and no break in the vessel wall when the lamina cribosa is punctured in accordance with the treatment procedure of the present invention. Further, there is shown in FIG. 5 an enucleated rabbit eye following in vivio laminar puncture via pars plana incision illustrating that no hemorrhaging occurred for such a procedure.

Moreover, macular fibers enter the optic nerve head along the periphery. Thus, with a puncture site(s) proximal or adjacent to the central retinal vein the damage to optic nerve fibers is limited to the central portion of the optic nerve. Consequently, there should be limited reduction in central vision that will be associated with the puncture itself. It should be recognized that the extremely poor visual acuity of potential patients that would be treated according to the method of the present invention, makes trauma to the optical nerve head not a significant limiting factor for conducting such a procedure.

The invention also includes device kits that comprise one or more puncturing devices 100 according to the present invention with or without the above-described surgical instruments 200/204, and infusion cannulas 202. In a more specific embodiment, the device kits include a plurality of such puncturing devices 100, puncturing devices having different configurations, sizes, and materials as well as puncturing devices having differently configured puncturing ends 112.

Although a preferred embodiment of the invention has been described using specific terms, such description is for illustrative purposes only, and it is to be understood that changes and variations may be made without departing from the spirit or scope of the following claims.

What is claimed is:

1. A method for increasing the luminal diameter of a retinal blood vessel being constricted by surrounding connective tissue comprising the step(s) of:
    puncturing the connective tissue surrounding the retinal blood vessel so as to create a perivascular space around at least a portion of the retinal blood vessel whereat it is being constricted.

2. The method of claim 1, wherein said puncturing is performed so as to create a perivascular space about the retinal blood vessel.

3. The method of claim 1, further comprising the steps of:
    providing a puncturing member; and
    positioning the puncturing member so a portion thereof is proximal the vessel wall of the retinal blood vessel during said step of puncturing.

4. The method of claim 1, wherein said puncturing includes forming one or more punctures in the connective tissue, each puncture having a width of about 400 microns or less.

5. The method of claim 4 wherein each puncture formed has a width in the range of one of about 200 to 400 microns or about 300 to 400 microns.

6. A method for treating an eye having a central retinal vein occlusion comprising the step(s) of:
    puncturing connective tissue of the lamina cribosa surrounding the retinal blood vessel so as to create a perivascular space around at least a portion of the retinal blood vessel at the level of the lamina cribosa.

7. The method of claim 6, wherein said puncturing is performed so as to crease a pen vascular space about the retinal blood vessel at the level of the lamina cribosa.

8. The method of claim 6, further comprising the steps of:
    providing a puncturing member; and
    positioning the puncturing member proximal the lamina cribosa and so a portion thereof is proximal the vessel wall of the retinal blood vessel during said step of puncturing.

9. The method of claim 7, wherein said puncturing includes forming one or more punctures in the connective tissue of the lamina cribosa, each puncture having a width of about 400 microns or less.

10. The method of claim 9 wherein each puncture formed has a width in the range of one of about 200 to 400 microns or about 300 to 400 microns.

* * * * *